US009518034B2

(12) United States Patent  (10) Patent No.: US 9,518,034 B2
Stoltz et al.  (45) Date of Patent: Dec. 13, 2016

(54) SYNTHESIS OF CHIRAL ENAMINONES, THEIR DERIVATIVES, AND BIOACTIVITY STUDIES THEREOF

(71) Applicant: California Institute of Technology, Pasadena, CA (US)

(72) Inventors: Brian M. Stoltz, San Marino, CA (US); Dennis A. Dougherty, South Pasadena, CA (US); Douglas Duquette, Los Angeles, CA (US); Noah Duffy, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 239 days.

(21) Appl. No.: 14/514,001

(22) Filed: Oct. 14, 2014

(65) Prior Publication Data

US 2015/0105552 A1  Apr. 16, 2015

Related U.S. Application Data

(60) Provisional application No. 61/890,708, filed on Oct. 14, 2013.

(51) Int. Cl.
 *C07D 295/116* (2006.01)
 *C07D 209/88* (2006.01)

(52) U.S. Cl.
 CPC ......... *C07D 295/116* (2013.01); *C07D 209/88* (2013.01)

(58) Field of Classification Search
 None
 See application file for complete search history.

(56) References Cited

U.S. PATENT DOCUMENTS

| 2,886,487 | A | 5/1959 | Kupferberg |
| 5,591,769 | A | 1/1997 | Himmelsbach et al. |
| 8,822,679 | B2 | 9/2014 | Stoltz et al. |
| 2010/0298293 | A1 | 11/2010 | Allerheiligen et al. |
| 2013/0267699 | A1 | 10/2013 | Stoltz et al. |

FOREIGN PATENT DOCUMENTS

| WO | WO-2009/013390 | 1/2009 |
| WO | WO-2009/153178 | 12/2009 |

OTHER PUBLICATIONS

Amat et al., "Enantioselective Synthesis of 3,3-Disubstituted Piperidine Derivatives by Enolate Dialkylation of Phenylglycinol-derived oxazolopiperidone Lactams," J. Org. Chem., 72:4431-4439 (2007).
Bach, T., "Regioselective Reducing Ring Opening of 2-(2-Hydroxyphenyl)-3-[(trimethylsilyl)oxy]oxetanes at the More Substituted C-2-Position", Liebigs. Ann. No. 7 (1997): 1529-1536.
Baussanne et al., "Diastereoselective Bis-Alkylation of Chiral Non-Racemic α,β-Unsaturated γ-Lactams," Tetrahedron Letters, 35(23):3931-3934 (1994).
Badillo et al., "Enantioselective synthesis of substituted oxindoles and spirooxindoles with applications in drug discovery," Current Opinion in Drug Discovery & Development, 13(6):758-776 (2010).
Behenna et al., "Enantioselective construction of quaternary N-heterocycles by palladium-catalysed decarboxylative allylic alkylation of lactams", Nature Chem. 2012, 4, 130.
Behenna et al., "Enantioselective Decarboxylative Alkylation Reactions: Catalyst Developement, Substrate Scope, and Mechanistic Studies", Chem. Eur. J. 2011, 17, 14199.
Behenna and Stoltz, "The Enantioselective Tsuji Allylation," J. Am. Chem. Soc., 126(46):15044-15045 (2004).
Bennett et al., "A Unified Approach to the Daucane and Sphenolobane Bicyclo[5.3.0]decane Core: Enantioselective Total Synthesis of Daucene, Daucenal, Epoxydaucenal B, and 14-para-Anisoyloxydauc-4,8-diene", Chem. Eur. J. 2013, 52, 17745.
Bennett et al., "Expanding Insight into Asymmetric Palladium-Catalyzed Allylic Alklation of N-Heterocyclic Molecules and Cyclic Ketones", Chem. Eur. J. 2013, 19, 4414.
Bennett et al., Synthesis of enantioenriched γ-quaternary cycloheptenones using a combined allylic alkyalation/Stork-Danheiser approach: preparation of mono-, bi-, and tricyclic systems, Org. Biomol. Chem. 2012, 10, 56.
Bobranski et al., Hydration of Phenyldiallylacetamide, 7, Bulletin De L'Academie Polonaise De Sciences, Serie Des Sciences, Chimiques, Geologiques Et Geographiques, pp. 399-401 (1959) (CAS Abstract).

(Continued)

*Primary Examiner* — Rebecca Anderson
*Assistant Examiner* — Po-Chih Chen
(74) *Attorney, Agent, or Firm* — Foley Hoag LLP; David P. Halstead

(57) ABSTRACT

This invention provides enantioenriched heterocyclic enaminone compounds with quaternary stereogenic centers and novel methods of preparing the compounds. Methods include the method for the preparation of a compound of formula (I):

(I)

comprising treating a compound of formula (II):

(II)

with a transition metal catalyst under alkylation conditions.

13 Claims, 1 Drawing Sheet

(56) References Cited

OTHER PUBLICATIONS

Bulman et al., "Short and Versatile Route to a Key Intermediate for Lactacystin Synthesis", Organic Letters, vol. 5, No. 3, pp. 353-355 (2003).
Coates et al., "Efficient synthesis of 3-substituted lactams using Meerwein Eschenmoser Claisen [3,3] sigmatropic rearrangements", 32(33) Tetrahedron Letts. 4199-202 (1991) (CAS Abstract).
Day et al., "The Catalytic Enantioselective Total Synthesis of (+)-Liphagal," Angew. Chem. Int. Ed., 50:6814-6818 (2011).
Desmaele et al., "Stereocontrolled Elaboration of Quaternary Carbon Centers through the Asymmetric Michael-Type Alkylation of Chiral Imines/Secondary Enamines: Enantioselective Synthesis of (+)-Vincamine," J. Org. Chem., 62:3890-3901 (1997).
Enders et al., "Asymmetric Electrophilic Substitutions at the α-Position of γ- and δ-Lactams," Eur. J. Org. Chem., pp. 4463-4477 (2001).
Enquist and Stoltz, "The total synthesis of (-)-cyanthiwigin F by means of double catalytic enantioselective alkylation," Nature, 453:1228-1231 (2008).
Enquist et al., "Total Syntheses of Cyanthiwigins B, F, and G", Chem. Eur. J. 2011, 17, 9957.
Ezquerra et al., "Stereoselective Double Alkylation of Ethyl N-Boc-pyroglutamate," J. Org. Chem., 59(15):4327-4331 (1994).
Fuji et al., "Addition-elimination strategy for asymmetric induction: a chiral sulfoxide as a leaving group", 31 (17) Tetrahedron Letts. 2419-22 (1990) (CAS abstract).
Gartshore et al., "Enantioselective Palladium-Catalyzed Decarboxylative Allylation of Carbazolones and Indolones: Formal Synthesis of (+)-Kopsihainanine A", Angew Chem. Int. Ed. 2013, 52, 4113.
Groaning and Meyers, "Chiral Non-Racemic Bicyclic Lactams. Auxiliary-Based Asymmetric Reactions," Tetrahedron, 56(549):9843-9873 (2000).
Helmchen and Pfaltz, "Phosphinooxazolines—A New Class of Versatile, Modular P,N-Ligands for Asymmetric Catalysis," Acc. Chem. Res., 33(6):336-345 (2000).
Hong et al., "Biosynthesis and Chemical Synthesis of Presilphiperfolanol Natural Products", Angew. Chem. Int. Ed. 2014, 53, 5248.
Hong et al., "Enantioselective Total Synthesis of the Reported Structures of (-)-9-epi-Presilphiperfolan-1-ol and (-)-Presilphiperfolan-1-ol: Structural Confirmation and Reassignment and Biosynthetic Insights", Angew. Chem. Int. Ed. 2012, 51, 9674.
Hong et al., "Palladium-catalyzed asymmetric alkylation in the synthesis of cyclopentanoid and cycloheptanoid core structures bearing all-carbon quaternary stereocenters", Tetrahedron 2011, 67, 10234.
Hong et al., "The Construction of All-Carbon Quaternary Stereocenters by Use of Pd-Catalyzed Asymmetric Allylic Alkylation Reactions in Total Synthesis", Eur. J. Org. Chem. 2013, 14, 2745.
Imao et al., "Easy Access to Esters with a Benzylic Quaternary Carbon Center from Diallyl Malonates by Palladium-Catalyzed Decarboxylative Allylation," J. Org. Chem., 72:1652-1658 (2007).
Jakubec et al., "Enantio- and diastereoselective Michael additions of C-succinimidyl esters to nitro olefins using cinchonine-derived bifunctional organocatalysts," Tetrahedron: Asymmetry, 22:1147-1155 (2011).
Jing et al., "Total Synthesis of (+)-Kopsihainanine A", Chem. Eur. J. 2012, 18, 6729.
Juaristi et al., Enantioselective synthesis of β-amino acids. Part 9: Preparation of enantiiopure α, α-disubstituted β-amino acids from 1-benzoyl-2(S)-tert-butyl-3-methylperhydropyrimidin-4-one1,2, Tetrahedron: Asymmetry, 9:3881-3888 (1998).
Keith et al., "The Reaction Mechanism of the Enantioselective Tsuji Allylation: Inner-Sphere and Outer-Sphere Pathways, Internal Rearrangements, and Asymmetric C-C Bond Formation", J. Am. Chem. Soc. 2012, 134, 19050.
Kim et al., An Asymmetric Synthesis of (+)-Isonitramine by 'Triple Allylic Strain-Controlled' Intramolecular SN2' Alkylation, Tetrahedron Letters, 37(9):1433-1434 (1996).
Li et al., "Enantioselective Palladium-Catalyzed Decarboxylative Allylation of Carbazolones: Total Synthesis of (-)-Aspidospermidine and (+)-Kopsihainanine A", Angew Chem. Int. Ed. 2013, 52, 4117.
Liu et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis", J. Am. Chem. Soc. 2013, 135, 10626.
Lu and Ma, "Metal-Catalyzed Enantioselective Allylation in Asymmetric Synthesis," Angew. Chem. Int. Ed., 47:258-297 (2008).
Ma et al., "Palladium-catalyzed decarboxylative allylic alkylation of diastereomeric β-ketoesters", Tetrahedron 2014, 70, 4208.
McDougal et al., "High-Throughput Screening of the Asymmetric Decarboxylative Alkylation Reaction of Enolate-Stabilized Enol Carbonates," Snylett, 11:1712-1716 (2010).
McDougal et al., "Rapid synthesis of an electron-deficient t-BuPHOX ligand: cross-coupling of aryl bromides with secondary phosphine oxides," Tetrahedron Letters, 51:5550-5554 (2010).
McFadden and Stoltz, "The Catalytic Enantioselective, Protecting Group-Free Total Synthesis of (+)-Dichroanone," J. Am. Chem. Soc., 128:7738-7739 (2006).
Mertes et al., "Glutarimides", J.Am.Pharma. Assoc. vol. 67, pp. 882-885, (1912-1977) (1958) (CAS Abstract).
Meyers et al., "Stereoselective Alkylations in Rigid Systems. Effect of Remote Substituents on π-Facial Additions to Lactam Enolates. Stereoelectronic and Steric Effects," J. Am. Chem. Soc., 120:7429-7438 (1998).
Mohr and Stoltz, "Enantioselective Tsuji Allylations," Chem. Asian J., 2:1476-1491 (2007).
Mohr et al., "Deracemization of Quaternary Stereocenters by Pd-Catalyzed Enantioconvergent Decarboxylative Allylation of Racemic β-Ketoesters," Angew.Chem. Int. Ed., 44:6924-6927 (2005).
Moss et al., "Catalytic Enantio- and Diastereoselective Alkylations with Cyclic Sulfamidates," Angew. Chem. Int. Ed., 49:568-571 (2010).
Ojima and Pei, "Asymmetric Synthesis with Chiral β-Lactams. Highly Stereoselective Alkylation and Aldol Reaction of a Chiral 3-Amino-4-Styryl-β-Lactam," Tetrahedrom Letters, 31(7):977-980 (1990).
Padwa et al., "A Novel Cycloaddition Reaction of α-Diazo-γ-amido Ketones Catalyzed by Rhodium (II) Acetate. Scope and Mechanistic Details of the Process", 61(7) J. Org. Chem. 2283-92 (1996) (CAS Abstract).
Park et al., "Highly Enantioselective Phase-Transfer Catalytic α-Alkylation of α-tert-Butoxycarbonyllactams: Construction of β-Quaternary Chiral Pyrrolidine and Piperidine Systems," Adv. Synth. Catal., 353:3313-3318 (2011).
Reeves et al., "Development of (Trimethylsilyl)ethyl Ester Protected Enolates and Applications in Palladium-Catalyzed Enantioselective Allylic Alkylation: Intermolecular Cross-Coupling of Functionalized Electrophiles", Org. Lett. 2014, 16, 2314.
Reeves, et al., "Enantioselective Construction of α-Quaternary Cyclobutanones by Catalytic Asymmetric Allylic Alkylation", Angew. Chem. Int. Ed. 2013, 52, 6718.
Rodriguez et al., "Carba Peptide Bond Surrogates/Different Approaches to Gly-(CH2-CH2)-D,L-XAA Pseudodipeptide Units", International Journal of Peptide and Protein Research, vol. 39, No. 3, pp. 273-277 (1992).
Schwarz and Meyers, "Tandem α-Cyano Enamine/Enolate Alkylations on Bicyclic Lactams: Asymmetric Carbocycle and Heterocycle Synthesis," J. Org. Chem., 63(5):1619-1629 (1998).
Seto et al., "Catalytic Enantioselective Alkylation of Substituted Dioxanone Enol Ethers: Ready Access to C(α)-Tetrasubstituted Hydroxyketones, Acids, and Esters," Angew. Chem. Int. Ed., 47:6873-6876 (2008).
Shibuya et al., "Enantioselective Synthesis of 5-6-7 Carbocyclic Core of the Gagunin Diterpenoids", Org. Lett. 2013, 15, 3480.

(56) References Cited

OTHER PUBLICATIONS

Streuff et al., "A palladium-catalysed enolate alkylation cascade for the formation of adjacent quaternary and tertiary sterocentres," Nature Chemistry, 2:192-196 (2010).

Takahashi et al., "Atropisomeric lactam chemistry: catalytic enantioselective synthesis, application to asymmetric enolate chemistry and synthesis of key intermediates for NET inhibitors," Tetrahedron, 66:288-296 (2010).

Tani et al., "A Facile and Modular Synthesis of Phosphinooxazoline Ligands," Organic Letters, 9(13):2529-2531 (2007).

Tari et al., "Recoverable *Cinchona* ammonium salts as organocatalysts in the enantioselective Michael addition of β-Keto esters," Tetrahedron: Asymmetry, 21:2872-2878 (2010).

Trost et al., "Enantioselective Synthesis of [alpha]-Tertiary Hydroxyaldehydes by Palladium-Catalyzed Asymmetric Allylic Alkylation of Enolates", Journal of the American Chemical Society, vol. 129, No. 2, pp. 282-283 (2007).

Trost and Brennan, "Asymmetric Synthesis of Oxindole and Indole Spirocyclic Alkaloid Natural Products," Synthesis, 18:3003-3025 (2009).

Trost, Barry M., "Asymmetric Allylic Alkylation, an Enabling Methodology," J. Org. Chem., 69(18):5813-5837 (2004).

Varea et al., "Asymmetric Synthesis. XXXV[1]. Synthesis of 2-Methyl 5-Substituted Piperidines from Chiral Non-racemic Lactams," Tetrahedron Letters, 36(7):1035-1038 (1995).

Vijn et al., "Highly Enantioselective Synthesis of a 2,3-Dihydroindole Mediated by N-Methylephedrine," Angew. Chem. Int. Ed. Engl., 23(2):165-166 (1984).

Weaver et al., "Transition Metal-Catalyzed Decarboxylatiave Allylation and Benzylation Reactions," Chem. Rev., 111:1846-1913 (2011).

White et al., "The Catalytic Asymmetric Total Synthesis of Elatol," J. Am. Chem. Soc., 130(3):810-811 (2008).

Zhou et al., "Catalytic Asymmetric Synthesis of Oxindoles Bearing a Tetrasubstituted Stereocenter at the C-3 Position," Adv. Synth. Catal., 352:1381-1407 (2010).

Search Report from International Patent Application No. PCT/US2012/043904 dated Feb. 1, 2013.

Written Opinion from International Patent Application No. PCT/US2012/043904 dated Feb. 1, 2013.

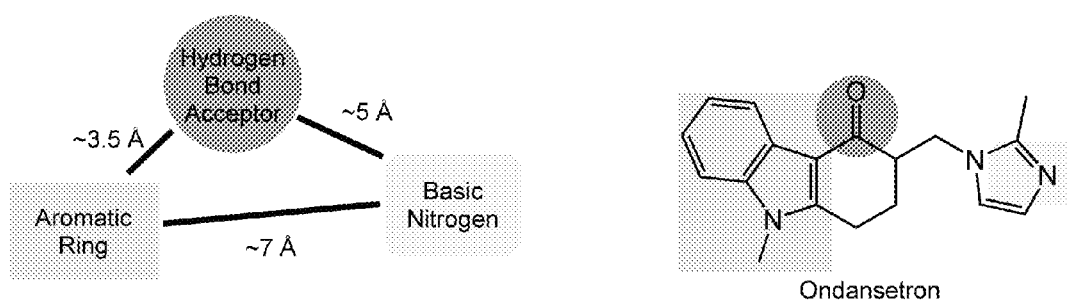

SYNTHESIS OF CHIRAL ENAMINONES, THEIR DERIVATIVES, AND BIOACTIVITY STUDIES THEREOF

RELATED APPLICATIONS

This application claims the benefit of U.S. Provisional Application 61/890,708 filed on Oct. 14, 2013, the content of which is incorporated herein by reference.

GOVERNMENT SUPPORT

This invention was made with government support under GM080269 awarded by the National Institutes of Health. The government has certain rights in the invention.

BACKGROUND OF THE INVENTION

Nitrogen-containing heterocycles are prevalent in numerous biologically active products that are the bases and templates for countless pharmaceuticals and other compounds used in many disciplines, including medicinal chemistry. Among the many pharmaceutical uses of nitrogen-containing heterocycles, many of these compounds have been identified as serotonin 5-HT$_3$ antagonists, including ondansetron, palonosetron, granisetron, tropisetron, and dolasetron, depicted below.

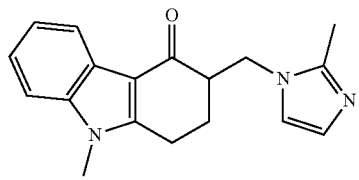

Ondansetron (GSK Zofran)
binding affinity = 4.9 nM

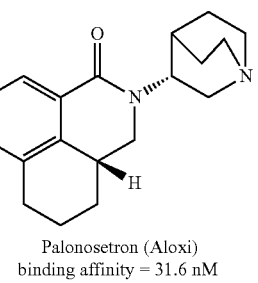

Palonosetron (Aloxi)
binding affinity = 31.6 nM

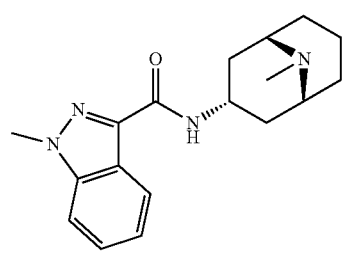

Granisetron (Roche Kytril)
binding affinity = 1.44 nM

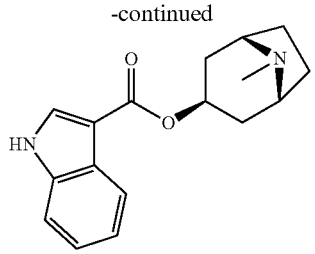

Tropisetron (Novartis Navoban)
binding affinity = 11 nM

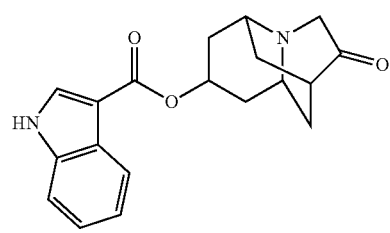

Dolasetron (Anzemet)
binding affinity = 20.03 nM

Often, one enantiomer of a nitrogen-containing heterocycle is primarily responsible for the biological activity of a racemate; the other enantiomer generally exhibits less or even no activity. In addition, different stereoisomers of a compound often exhibit other differences in biological activity. Accordingly, a stereo- and enantioselective synthesis of a target compound is typically a more efficient way to produce chiral pharmaceuticals or other compounds. However, stereo- and enantioselective syntheses of many nitrogen-containing heterocyclic compounds can be difficult. While some stereoselective methods for the synthesis of certain nitrogen-containing heterocycles and their cyclic amine derivatives are known, fewer enantioselective methods exist. Additionally, many of these stereoselective methods use chiral auxiliaries specific to particular functional groups, which is less mass-efficient and/or cost-effective.

The 5-HT$_3$ receptor is a membrane-bound ligand-gated ion channel whose natural ligand is serotonin. The inhibitors depicted above are highly selective against other 5-HT receptor subtypes, and act by preventing excitation of the vagus nerve in the medulla oblongata, which induces vomiting. These drugs are commonly administered in combination with chemotherapeutics to reduce nausea and vomiting.

The pharmacophore for 5-HT$_3$ receptor antagonists consists of three chemical moieties, as depicted in FIG. 1. The N-containing heteroaromatic moiety is proposed to participate in cation-π interaction with a protonated arginine residue of the protein. The basic nitrogen moiety, in its protonated form, is proposed to participate in a cation-π interaction with tyrosine and tryptophan residues of the protein. The hydrogen bond acceptor, which in ondansetron is the carbonyl group, is proposed to participate in a hydrogen bonding interaction with a network of bound water molecules.

There is a need for methods that would allow access to chemical scaffolds having a basic structural analogy to the ondansetron pharmacophore, particularly enantioselective methods to provide enantioenriched products.

SUMMARY OF THE INVENTION

In one aspect, the present invention provides methods for the preparation of a compound of formula (I):

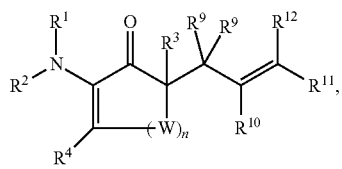
(I)

comprising treating a compound of formula (II):

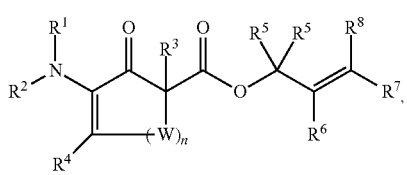
(II)

with a transition metal catalyst under alkylation conditions, wherein, as valence and stability permit, $R^1$ and $R^2$ are independently hydrogen or optionally substituted alkyl, aryl, aralkyl, heteroaryl, heteroaralkyl, alkenyl, or alkynyl; or $R^1$ and $R^2$ are taken together to form an optionally substituted heterocyclic ring;

$R^3$ is substituted or unsubstituted hydrogen, alkyl, aralkyl, aryl, heteroaralkyl, heteroaryl, alkenyl, alkynyl, or halo;

$R^4$ is hydrogen, halogen, alkyl, aralkyl, aryl, heteroaralkyl, heteroaryl, alkenyl, or alkynyl;

$R^5$, $R^6$, $R^7$, $R^8$, $R^9$, $R^{10}$, $R^{11}$, and $R^{12}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;

W is $CR^{13}R^{13}$, O, S, or $NR^{14}$;

$R^{13}$ is selected, independently for each occurrence, from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;

$R^{14}$ is independently selected for each occurrence from hydrogen, alkyl, aryl, aralkyl, heteroaryl, heteroaralkyl, alkenyl, or alkynyl;

wherein $R^2$ and $R^4$ may combine with the atoms to which they are attached to form an optionally substituted 4-9 membered heterocyclic ring, $R^4$ and an occurrence of $R^{13}$ may combine with the carbons to which they are attached to form an optionally substituted 3-8 membered ring, $R^4$ and an occurrence of $R^{14}$ may combine with the atoms to which they are attached to form an optionally substituted 4-8 membered ring, two occurrences of $R^{13}$ may combine with the carbons to which they are attached to form a 3-8 membered ring, or an occurrence of $R^{13}$ and an occurrence of $R^{14}$ may combine with the atoms to which they are attached to form an optionally substituted 4-8 membered heterocyclic ring; and n is an integer from 1-4.

In another aspect, the invention provides compounds of formula (I):

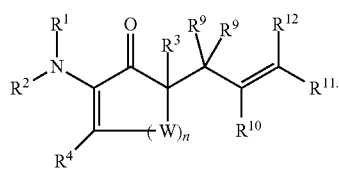
(I)

In another aspect, the invention provides compounds of formula (II):

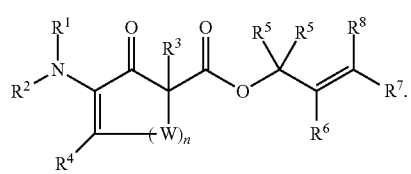
(II)

BRIEF DESCRIPTION OF THE DRAWINGS

These and other features and advantages of the present invention will be better understood by reference to the following detailed description when considered in conjunction with the following drawing, in which:

FIG. 1 shows the pharmacophore of 5-HT$_3$ receptor antagonists such as ondansetron.

DETAILED DESCRIPTION OF THE INVENTION

I. Definitions

The definitions for the terms described below are applicable to the use of the term by itself or in combination with another term.

The term "acyl" is art-recognized and refers to a group represented by the general formula hydrocarbyl-C(O)—, preferably alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

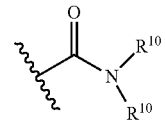

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

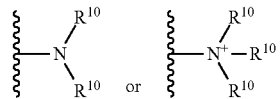

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group. An aralkyl group is connected to the rest of the molecule through the alkyl component of the aralkyl group.

The term "aryl" as used herein include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety The term "carbamate" is art-recognized and refers to a group

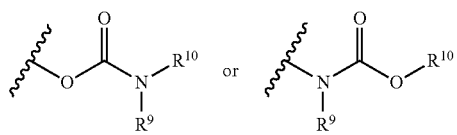

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO₂—$R^{10}$, wherein $R^{10}$ represents a hydrocarbyl group.

The term "carboxyl", as used herein, refers to a group represented by the formula —CO₂H.

The term "ester", as used herein, refers to a group —C(O)OR¹⁰ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto. A "silyl ether" refers to a silyl group linked through an oxygen to a hydrocarbyl group. Exemplary silyl ethers include —OSi(CH$_3$)$_3$ (—OTMS), —OSi(CH$_3$)$_2$t-Bu (—OTBS), —OSi(Ph)$_2$t-Bu (—OTBDPS), and —OSi(iPr)$_3$ (—OTIPS).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

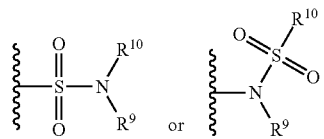

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

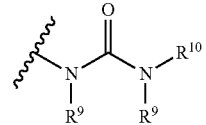

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

II. Description of the Invention

This invention is based on the surprising discovery that catalytic decarboxylative allylic alkylation reactions in en-2-aminone substrates generate en-2-aminone products with α-all-carbon quaternary stereocenters and proceed in high enantioselectivities that are unprecedented for other carbocyclic substrates that lack substitution on the allylic fragment. The decarboxylative allylic alkylation reaction is catalyzed by a transition metal catalyst and a chiral ligand, and the products can be quickly and efficiently elaborated into complex products exhibiting biological activity.

For example, en-2-aminone products of the decarboxylative allylic alkylation can be converted into carbazolone products bearing a quaternary center. Such carbazolone products have a core structure analogous to known serotonin 5-$HT_3$ receptor antagonists, such as ondansetron. The methods of the present invention provide access to compounds that inhibit 5-$HT_3$.

According to embodiments of the present invention, a wide range of structurally-diverse, functionalized nitrogen-containing compounds are prepared by a stereoselective method of palladium-catalyzed enantioselective enolate allylic alkylation. This chemistry is important to the synthesis of bioactive alkaloids, and the transformation is useful for the construction of novel building blocks for medicinal and polymer chemistry. Indeed, in some embodiments of the present invention, these novel building blocks include nitrogen-containing compounds useful as precursors to (or reactants leading to the preparation of) numerous biologically active and important natural and pharmaceutical products. While embodiments of the present invention are directed to the novel building blocks achieved from the transition-metal catalyzed allylic alkylation reaction, other embodiments of the present invention are directed to novel nitrogen-containing substrates used in the transition-metal catalyzed allylic alkylation reaction to form the building blocks.

Indeed, in some embodiments of the present invention, a method of making a building block compound comprises reacting a substrate compound with a ligand in the presence of a palladium-based catalyst and a solvent. The palladium-based catalysts, ligands and solvents useful in this reaction are described in more detail below in Section III.

III. Compounds and Methods of the Invention

In one aspect, the present invention provides a method for preparing a compound of formula (I):

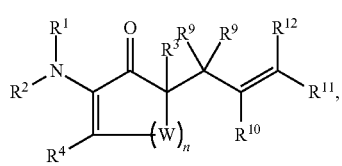

(I)

comprising treating a compound of formula (II):

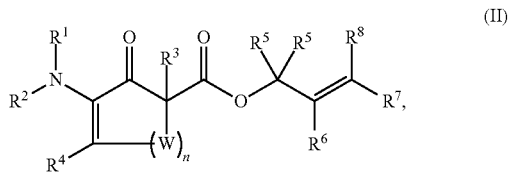

(II)

with a transition metal catalyst under alkylation conditions, wherein, as valence and stability permit, $R^1$ and $R^2$ are independently hydrogen or optionally substituted alkyl, aryl, aralkyl, heteroaryl, heteroaralkyl, alkenyl, or alkynyl; or $R^1$ and $R^2$ are taken together to form an optionally substituted heterocyclic ring;

$R^3$ is substituted or unsubstituted hydrogen, alkyl, aralkyl, aryl, heteroaralkyl, heteroaryl, alkenyl, alkynyl, or halo;

$R^4$ is hydrogen, halogen, alkyl, aralkyl, aryl, heteroaralkyl, heteroaryl, alkenyl, or alkynyl;

$R^5$, $R^6$, $R^7$, $R^8$, $R^9$, $R^{10}$, $R^{11}$, and $R^{12}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;

W is $CR^{13}R^{13}$, O, S, or $NR^{14}$;

$R^{13}$ is independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;

$R^{14}$ is independently selected for each occurrence from hydrogen, alkyl, aryl, aralkyl, heteroaryl, heteroaralkyl, alkenyl, or alkynyl;

wherein $R^2$ and $R^4$ may combine with the atoms to which they are attached to form an optionally substituted 4-9 membered heterocyclic ring, $R^4$ and an occurrence of $R^{13}$ may combine with the carbons to which they are attached to form an optionally substituted 3-8 membered ring, $R^4$ and an occurrence of $R^{14}$ may combine with the atoms to which they are attached to form an optionally substituted 4-8 membered ring, two occurrences of $R^{13}$ (e.g., one occurrence of $R^{13}$ attached to one carbon and the other occurrence of $R^{13}$ attached to another carbon) may combine with the carbons to which they are attached to form a 3-8 membered ring, or an occurrence of $R^{13}$ and an occurrence of $R^{14}$ may combine with the atoms to which they are attached to form an optionally substituted 4-8 membered heterocyclic ring; and n is an integer from 1-4.

In certain embodiments, $R^5$, $R^6$, $R^7$, $R^8$, $R^9$, $R^{10}$, $R^{11}$, and $R^{12}$ are independently selected for each occurrence from hydrogen, halogen, cyano, alkyl, alkoxyl, alkylthio, amide, amine, aryloxy, and arylalkoxy. In certain embodiments, $R^5$, $R^6$, $R^7$, $R^8$, $R^9$, $R^{10}$, $R^{11}$, and $R^{12}$ are independently selected for each occurrence from hydrogen and alkyl. In certain embodiments, $R^5$, $R^6$, $R^7$, $R^8$, $R^9$, $R^{10}$, $R^{11}$, and $R^{12}$ are each hydrogen.

In certain embodiments, $R^3$ is selected from substituted or unsubstituted alkyl, aralkyl, aryl, heteroaralkyl, heteroaryl, alkenyl, alkynyl, and halo. In certain embodiments, $R^3$ is hydrogen. In certain embodiments, $R^3$ is selected from optionally substituted alkyl, aralkyl, and aryl. In certain embodiments, the optionally substituted alkyl is an alkyl group optionally substituted by halogen, haloalkyl, hydroxyl, carboxyl, alkoxycarbonyl, formyl, acyl, thioester, thioacetate, thioformate, alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or aromatic or heteroaromatic moiety. In certain embodiments, $R^3$ is an optionally substituted alkyl such as haloalkyl, hydroxyalkyl, or alkyl substituted by a silyl ether, cyano, ester, or ketone. In certain embodiments, $R^3$ is selected from optionally substituted alkyl, aryl, aralkyl, haloalkyl, and hydroxyalkyl.

In certain embodiments, W at each occurrence is $CR^{13}R^{13}$ and n is an integer from 1-3. In certain embodiments, W at each occurrence is $CR^{13}R^{13}$ and n is 1 or 2. In certain embodiments, $R^{13}$ is independently for each occurrence selected from hydrogen, halogen, cyano, alkyl, alkylthio, amide, amine, aryloxy, and arylalkoxy.

In certain embodiments, $R^1$ and $R^2$ are independently optionally substituted alkyl, aralkyl, heteroaralkyl, alkenyl, or alkynyl. In certain embodiments, $R^1$ and $R^2$ are taken together to form an optionally substituted heterocyclic ring. In certain embodiments, the heterocyclic ring is a 3-10 membered monocyclic or polycyclic ring system, and has one or more heteroatoms. In exemplary embodiments, the heterocyclic ring is substituted or unsubstituted piperidine, morpholine, pyrrolidine, a fully- or partially-hydrogenated quinolone or isoquinoline, indoline, indole, or pyrrole.

In certain embodiments, no two adjacent occurrences of W are O, no two adjacent occurrences of W are S, and no two adjacent occurrences of W are O and S.

In certain embodiments, the invention relates to a compound of formula (I),

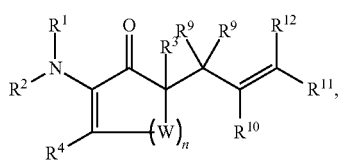

(I)

or a tautomer and/or salt thereof, wherein:
$R^1$ and $R^2$ are independently hydrogen or optionally substituted alkyl, aryl, aralkyl, heteroaryl, heteroaralkyl, alkenyl, or alkynyl; or
$R^1$ and $R^2$ are taken together to form an optionally substituted heterocyclic ring;
$R^3$ is substituted or unsubstituted hydrogen, alkyl, aralkyl, aryl, heteroaralkyl, heteroaryl, alkenyl, alkynyl, or halo;
$R^4$ is hydrogen, halogen, alkyl, aralkyl, aryl, heteroaralkyl, heteroaryl, alkenyl, or alkynyl;
$R^9$, $R^{10}$, $R^{11}$, and $R^{12}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;
W is $CR^{13}R^{13}$, O, S, or $NR^{14}$;
$R^{13}$ is independently selected from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;
$R^{14}$ is independently selected for each occurrence from hydrogen, alkyl, aryl, aralkyl, heteroaryl, heteroaralkyl, alkenyl, or alkynyl;
wherein $R^2$ and $R^4$ may combine with the atoms to which they are attached to form an optionally substituted 4-9 membered heterocyclic ring, $R^4$ and an occurrence of $R^{13}$ may combine with the carbons to which they are attached to form an optionally substituted 3-8 membered ring, $R^4$ and an occurrence of $R^{13}$ may combine with the carbons to which they are attached to form an optionally substituted 4-8 membered ring, two occurrences of $R^{13}$ (e.g., one occurrence of $R^{13}$ attached to one carbon and the other occurrence of $R^{13}$ attached to another carbon) may combine with the carbons to which they are attached to form a 3-8 membered ring, or an occurrence of $R^{13}$ and an occurrence of $R^{14}$ may combine with the atoms to which they are attached to form an optionally substituted 4-8 membered heterocyclic ring; and
n is an integer from 1-4.

In certain embodiments, $R^9$, $R^{10}$, $R^{11}$, and $R^{12}$ are independently selected for each occurrence from hydrogen, halogen, cyano, alkyl, alkoxyl, alkylthio, amide, amine, aryloxy, and arylalkoxy. In certain embodiments, $R^9$, $R^{10}$, $R^{11}$, and $R^{12}$ are independently selected for each occurrence from hydrogen and alkyl. In certain embodiments, $R^9$, $R^{10}$, $R^{11}$, and $R^{12}$ are each hydrogen.

In certain embodiments, $R^3$ is selected from substituted or unsubstituted alkyl, aralkyl, aryl, heteroaralkyl, heteroaryl, alkenyl, alkynyl, and halo. In certain embodiments, $R^3$ is hydrogen. In certain embodiments, $R^3$ is selected from optionally substituted alkyl, aralkyl, and aryl. In certain embodiments, the optionally substituted alkyl is an alkyl group optionally substituted by halogen, haloalkyl, hydroxyl, carboxyl, alkoxycarbonyl, formyl, acyl, thioester, thioacetate, thioformate, alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or aromatic or heteroaromatic moiety. In certain embodiments, $R^3$ is an optionally substituted alkyl such as haloalkyl, hydroxyalkyl, or alkyl substituted by a silyl ether, cyano, ester, or ketone. In certain embodiments, $R^3$ is selected from optionally substituted alkyl, aryl, aralkyl, haloalkyl, and hydroxyalkyl.

In certain embodiments, W at each occurrence is $CR^{13}R^{13}$ and n is an integer from 1-3. In certain embodiments, W at each occurrence is $CR^{13}R^{13}$ and n is 1 or 2. In certain embodiments, $R^{13}$ is independently at each occurrence selected from hydrogen, halogen, cyano, alkyl, alkylthio, amide, amine, aryloxy, and arylalkoxy.

In certain embodiments, $R^1$ and $R^2$ are independently optionally substituted alkyl, aralkyl, heteroaralkyl, alkenyl, or alkynyl. In certain embodiments, $R^1$ and $R^2$ are taken together to form an optionally substituted heterocyclic ring. In certain embodiments, the heterocyclic ring is a 3-10 membered monocyclic or polycyclic ring system, and has one or more heteroatoms. In example embodiments, the heterocyclic ring is substituted or unsubstituted piperidine, morpholine, pyrrolidine, a fully- or partially-hydrogenated quinolone or isoquinoline, indoline, indole, or pyrrole.

In certain embodiments, no two adjacent occurrences of W are O, no two adjacent occurrences of W are S, and no two adjacent occurrences of W are O and S.

In certain embodiments, the invention relates to a compound of formula (I), wherein the compound is enantioenriched.

In certain embodiments, the invention relates to a compound of formula (II),

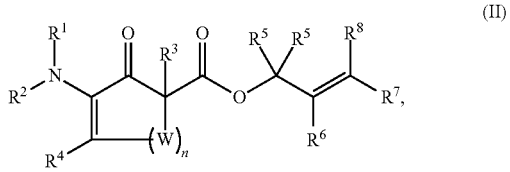

or a tautomer and/or salt thereof, wherein $R^1$-$R^8$, W, and n are defined above.

Transition Metal Catalysts

Preferred transition metal catalysts of the invention are complexes of transition metals wherein the metal is selected from Groups 6, 8, 9 and 10 in the periodic table. In preferred embodiments, the metal of the transition metal catalyst is selected from molybdenum, tungsten, iridium, rhenium, ruthenium, nickel, platinum, and palladium. In more preferred embodiments, the transition metal catalyst comprises a transition metal selected from palladium, nickel, and platinum, most preferably palladium.

In certain embodiments of the invention, the transition metal complex utilized in the reaction includes a transition metal that has a low oxidation state, typically (0) or (I). A low oxidation state enables the metal to undergo oxidative addition to the substrate. It should be appreciated that the air- and moisture-sensitivity of many such complexes of transition metals will necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use.

Exemplary transition metal catalysts include, without limitation, $Mo(CO)_6$, $Mo(MeCN)_3(CO)_3$, $W(CO)_6$, $W(MeCN)_3(CO)_3$, $[Ir(1,5\text{-cyclooctadiene})Cl]_2$, $[Ir(1,5\text{-cyclooctadiene})Cl]_2$, $[Ir(1,5\text{-cyclooctadiene})Cl]_2$, $Rh(PPh_3)_3Cl$, $[Rh(1,5\text{-cyclooctadiene})Cl]_2$, $Ru(pentamethylcyclopentadienyl)(MeCN)_3PF_6$, $Ni(1,5\text{-cyclooctadiene})_2$, $Ni[P(OEt)_3]_4$, tris(dibenzylideneacetone)dipalladium(0), tris(dibenzylideneacetone)dipalladium(0)-chloroform adduct, bis(4-methoxybenzylidene)acetone)dipalladium(0), $Pd(OC(=O)CH_3)_2$, $Pd(3,5\text{-dimethyoxy-dibenzylideneacetone})_2$, $PdCl_2(R^{23}CN)_2$; $PdCl_2(PR^{24}R^{25}R^{26})_2$; $[Pd(\eta^3\text{-allyl})Cl]_2$; and $Pd(PR^{24}R^{25}R^{26})_4$, wherein $R^{23}$, $R^{24}$, $R^{25}$, and $R^{26}$ are independently selected from hydrocarbyl, substituted hydrocarbyl, heteroatom-containing hydrocarbyl, and substituted heteroatom-containing hydrocarbyl. In particular embodiments, the transition metal catalyst tris(dibenzylideneacetone)dipalladium, $Pd_2(dba)_3$, or bis(4-methoxybenzylidene)acetone)dipalladium, $Pd_2(pmdba)_3$, is preferred.

To improve the effectiveness of the catalysts discussed herein, additional reagents may be employed as needed, including, without limitation, salts, solvents, and other small molecules. Preferred additives include $AgBF_4$, $AgOSO_2CF_3$, $AgOC(=O)CH_3$, and bipyridine. These additives are preferably used in an amount that is in the range of about 1 equivalent to about 5 equivalents relative to the amount of the catalyst.

A low oxidation state of a transition metal, i.e., an oxidation state sufficiently low to undergo oxidative addition, can also be obtained in situ, by the reduction of transition metal complexes that have a high oxidation state. Reduction of the transition metal complex can be achieved by adding nucleophilic reagents including, without limitation, $NBu_4OH$, tetrabutylammonium difluorotriphenylsilicate (TBAT), tetrabutylammonium fluoride (TBAF), 4-dimethylaminopyridine (DMAP), $NMe_4OH(H_2O)_5$, KOH/1,4,7,10,13,16-hexaoxacyclooctadecane, EtONa, TBAT/trimethyl-(2-methyl-cyclohex-1-enyloxy)-silane, and mixtures thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

In certain embodiments, a Pd(II) complex can be reduced in situ to form a Pd(0) catalyst. Exemplary transition metal complexes that may be reduced in situ, include, without limitation, allylchloro[1,3-bis(2,6-di-i-propylphenyl)imidazol-2-ylidene]palladium(II), ([2S,3S]-bis[diphenylphosphino]butane)($\eta^3$-allyl)palladium(II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBu-PHOX)(allyl)]$PF_6$), and cyclopentadienyl($\eta^3$-allyl) palladium(II), with [Pd(s-tBu-PHOX)(allyl)]$PF_6$ and cyclopentadienyl($\eta^3$-allyl)palladium(II) being most preferred.

In certain embodiments, the transition metal is palladium. In certain embodiments, the transition metal catalyst is a dimer of a transition metal. Exemplary dimeric transition metal catalysts include $Pd_2(dba)_3$ and $Pd_2(pmdba)_3$. In certain preferred embodiments, the transition metal catalyst is $Pd_2(dba)_3$ or $Pd_2(pmdba)_3$. In embodiments of the method wherein the transition metal catalyst is a dimer, the amount of total transition metal present in the reaction is twice the amount of the transition metal catalytic complex.

Accordingly, when describing the amount of transition metal catalyst used in the methods of the invention, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, palladium) by the moles of the substrate present in a given reaction. For example, in a reaction that uses 5 mol % dimeric catalyst (e.g, $Pd_2(dba)_3$), this amount of transition metal catalyst can be alternatively expressed as 10 mol % total transition metal (e.g., Pd(0)).

In certain embodiments, the transition metal catalyst is present under the conditions of the reaction from an amount of about 0.1 mol % to about 20 mol % total palladium relative to the substrate, which is the compound of formula (II). In certain embodiments, the catalyst loading is from about 0.5 mol % to about 10 mol % total palladium relative to the substrate. For example, in certain embodiments, the catalyst loading is about 0.5 mol %, about 1 mol %, about 2 mol %, about 3 mol %, about 5 mol %, about 6 mol %, about 8 mol %, about 9 mol %, or about 10 mol % total palladium.

Ligands

One aspect of the invention relates to the enantioselectivity of the methods. Enantioselectivity results from the use of chiral ligands during the allylic alkylation reaction. Without being bound by theory, the asymmetric environment that is created around the metal center by the presence of chiral ligands produces an enantioselective reaction. The chiral ligand forms a complex with the transition metal, thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention.

Once coordinated to the transition metal center, the chiral ligand influences the orientation of other molecules as they interact with the transition metal catalyst. Coordination of the metal center with a π-allyl group and reaction of the substrate with the π-allyl-metal complex are dictated by the presence of the chiral ligand. The orientation of the reacting species determines the stereochemistry of the products.

Chiral ligands of the invention may be bidentate or monodentate or, alternatively, ligands with higher denticity (e.g., tridentate, tetradentate, etc.) can be used. Preferably, the ligand will be substantially enantiopure. By "enantiopure" is meant that only a single enantiomer is present. In many cases, substantially enantiopure ligands can be purchased from commercial sources, obtained by successive recrystallizations of an enantioenriched substance, or by other suitable means for separating enantiomers.

Exemplary chiral ligands may be found in U.S. Pat. No. 7,235,698, the entirely of which is incorporated herein by reference. In certain embodiments, the chiral ligand is an enantioenriched phosphine ligand. In certain embodiments, the enantioenriched phosphine ligand is a P,N-ligand such as a phosphinooxazoline (PHOX) ligand. Preferred chiral ligands of the invention include the PHOX-type chiral ligands such as (R)-2-[2-(diphenylphosphino)phenyl]-4-isopropyl-2-oxazoline, (R)-2-[2-(diphenylphosphino)phenyl]-4-phenyl-2-oxazoline, (S)-2-[2-(diphenylphosphino)phenyl]-4-benzyl-2-oxazoline, (S)-2-[2-(diphenylphosphino)phenyl]-4-tert-butyl-2-oxazoline ((S)-t-BuPHOX) and (S)-2-(2-(bis(4-(Trifluoromethyl)phenyl)phosphino)-5-(trifluoromethyl)phenyl)-4-(tert-butyl)-4,5-dihydrooxazole ((S)—(CF$_3$)$_3$-t-BuPHOX). In preferred embodiments, the PHOX type chiral ligand is selected from (S)-t-BuPHOX and (S)—(CF$_3$)$_3$-t-BuPHOX). The ligand structures are depicted below.

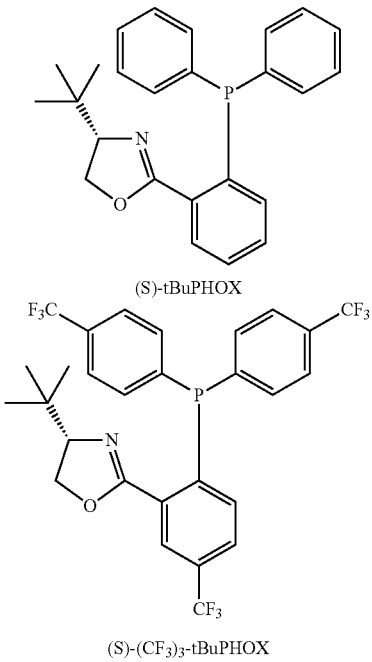

Generally, the chiral ligand is present in an amount in the range of about 0.75 equivalents to about 10 equivalents relative to the amount of total metal from the catalyst, preferably in the range of about 0.75 to about 5 equivalents relative to the amount of total metal from the catalyst, and most preferably in the range of about 0.75 to about 1.25, such as about 1.25 equivalents relative to the amount of total metal from the catalyst. Alternatively, the amount of the chiral ligand can be measured relative to the amount of the substrate.

In certain embodiments, the ligand is present under the conditions of the reaction from an amount of about 0.25 mol % to about 25 mol % relative to the substrate, which is the compound of formula (II). The amount of ligand present in the reaction is alternatively referred to herein as "ligand loading" and is expressed as a percentage that is calculated by dividing the moles of ligand by the moles of the substrate present in a given reaction. In certain embodiments, the ligand loading is from about 1 mol % to about 15 mol %. For example, in certain embodiments, the ligand loading is about 1.25 mol %, about 2.5 mol %, about 5 mol %, about 6 mol %, about 7.5 mol %, about 10 mol %, or about 12 mol %. In certain embodiments, the ligand is in excess of the transition metal catalyst. In certain embodiments, the ligand loading is about 1.25 times the transition metal catalyst loading. In embodiments in which the transition metal catalyst is a dimer, the ligand loading is about 2.5 times the loading of the dimeric transition metal catalyst.

Where a chiral ligand is used, the reactions of the invention may enrich the stereocenter bearing $R^3$ in the product relative to the enrichment at this center, if any, of the starting material. In certain embodiments, the chiral ligand used in the methods of the invention yields a compound of formula (I) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R)

enantiomer, then the ee of the compound is (98−2)/(98+2), or 96%. In certain embodiments, the compound of formula (I) has about 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In certain embodiments, the compound of formula (I) is enantioenriched. In certain embodiments, the compound of formula (I) is enantiopure. In embodiments where the starting material has more than one stereocenter, reactions of the invention may enrich the stereocenter bearing $R^3$ relative to the enrichment at this center, if any, of the starting material, and substantially independently of the stereochemical disposition/enrichment of any other stereocenters of the molecule. For example, a product of the methods described herein may have 30% de or greater, 40% de or greater, 50% de or greater, 60% de or greater, 70% de or greater, 80% de or greater, 90% de or greater, 95% de or greater, or even 98% de or greater at the stereocenter of the product bearing $R^1$.

In certain embodiments, the invention also relates to methods that utilize an achiral ligand. Exemplary achiral ligands include triphenylphosphine, tricyclohexylphosphine, tri-(ortho-tolyl)phosphine, trimethylphosphite, and triphenylphosphite.

Alkylation Conditions

In certain embodiments, the methods of the invention include treating a compound of formula (II) with a transition metal catalyst under alkylation conditions. In certain embodiments, alkylation conditions of the reaction include one or more organic solvents. In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclic ethers such as optionally substituted tetrahydrofuran and dioxane, acyclic ethers such as dimethoxyethane, diethyl ether, methyl tertbutyl ether, and cyclopentyl methyl ether, acetonitrile, isobutyl acetate, ethyl acetate, isopropyl acetate, or combinations thereof. In certain preferred embodiments, the solvent is toluene, methyl tertbutyl ether, cyclopentyl methyl ether, 2-methyltetrahydrofuran, isobutyl acetate, ethyl acetate, or isopropyl acetate. In certain other preferred embodiments, the solvent is ethyl acetate.

In certain embodiments, alkylation conditions of the reaction include a reaction temperature. In certain embodiments, the reaction temperature is ambient temperature (about 20° C. to about 26° C.). In certain embodiments, the reaction temperature is higher than ambient temperature, such as, for example, about 30° C., about 35° C., about 40° C., about 45° C., about 50° C., about 55° C., or about 60° C. In certain embodiments, the reaction temperature is lower than ambient temperature, such as, for example, about 0° C.

In certain embodiments, instruments such as a microwave reactor may be used to accelerate the reaction time. Pressures range from atmospheric to pressures typically used in conjunction with supercritical fluids, with the preferred pressure being atmospheric.

IV. Further Reactions of Products Generated by the Methods of the Invention

In certain embodiments, the invention includes methods for the preparation of a compound of formula (I),

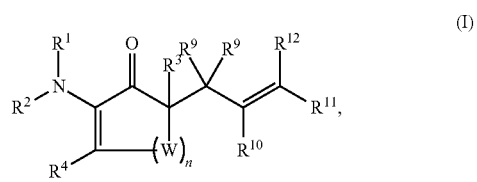

wherein $R^1$-$R^4$, $R^9$-$R^{12}$, W, and n are defined above.

As demonstrated in Example 3, compounds of formula (I) can be elaborated into complex products through the application of further chemical transformations. In certain embodiments, these complex products have structural similarities to biologically- or pharmaceutically-relevant products. In certain embodiments, these complex products are themselves biologically- or pharmaceutically-relevant products.

In an example embodiments, hydrolysis of the enamine group of formula (I) provides an enol, which may alternatively exist in its tautomeric form as a 1,2-diketone, as shown in equation (i) below. Conditions for hydrolysis include treating the compound of formula (I) with acidified water. Other conditions for hydrolysis may be selected, for example, when the compound of formula (I) is determined to contain a functional group that would not tolerate acidic conditions. Such alternative hydrolysis conditions are known to persons of ordinary skill in the art.

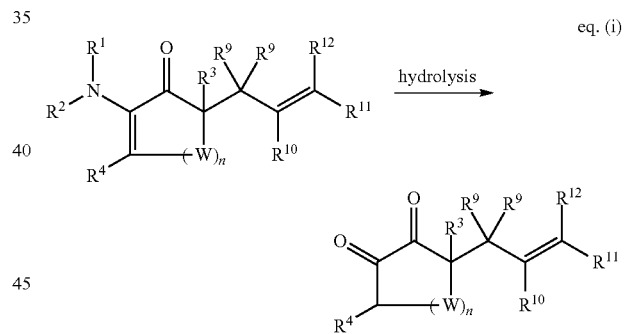

eq. (i)

In another embodiment, a compound of formula (I) reacts with an electrophile to form a product as shown in equation (ii) below:

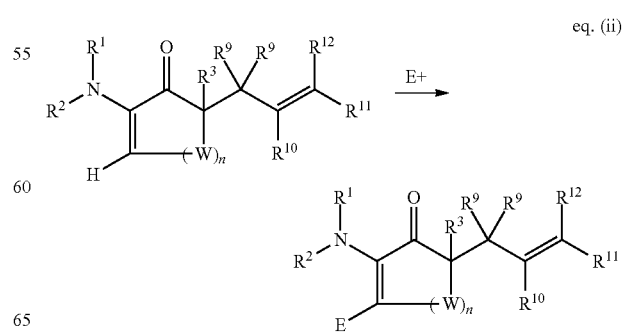

eq. (ii)

In certain embodiments, the electrophile is an electrophilic halogen source, such as N-bromosuccinimide, N-chlorosuccinimide, N-iodosuccinimide, bromine, or iodine. In certain embodiments, the electrophile is an electrophilic alkylating agent such as methyl iodide or methyl fluorosulfonate.

In certain embodiments, a compound of formula (I) reacts with a hydrazine derivative, for example, (hydrocarbyl) hydrazine as shown in equation (iii) below:

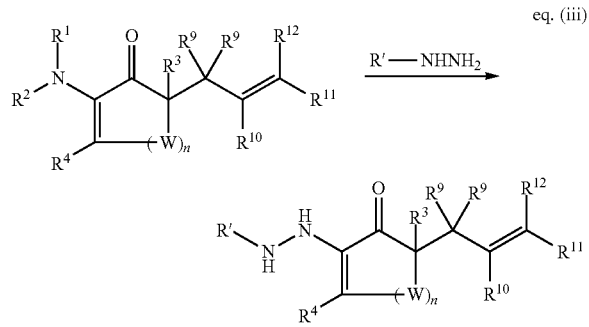

eq. (iii)

wherein $R^1$-$R^4$, $R^9$-$R^{12}$, W, and n are defined above, and R' is a hydrocarbyl group. In certain embodiments, R' is optionally substituted aryl or heteroaryl. In embodiments wherein R' is optionally substituted aryl or heteroaryl, a Fischer indole synthesis may convert the hydrazine to an indole, as exemplified below in equation (iv):

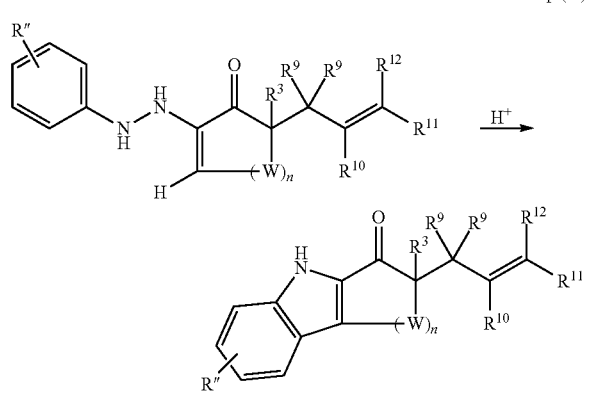

eq. (iv)

Conditions for a Fischer indole synthesis may be selected, for example, based upon stability of particular groups in the starting material. Selection of reaction conditions is well within the purview of a person of ordinary skill in the art of the invention.

In certain embodiments, the Fischer indole synthesis generates a compound of formula (III):

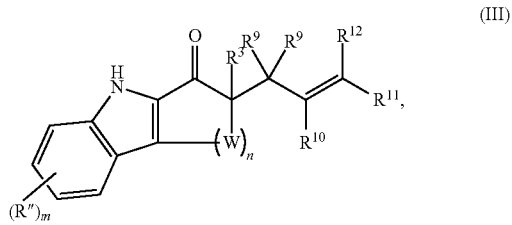

(III)

wherein $R^3$, $R^9$-$R^{12}$, W, W and n are defined as above, m is an integer from 0-4, and R" is an optional substituent on the aryl group. R" can include alkyl, alkoxyl, aryl, aralkyl, heteroaryl, heteroaralkyl, amino, alkylamino, alkenyl, alkynyl, halogen, hydroxyl, cyano, or, two or more adjacent instances of R" can be an optionally substituted aryl or heteroaryl ring.

V. Biological Activity of Compounds Derived by the Methods of the Invention

In certain embodiments, the compounds of formula (I), or compounds derived from formula (I) (such as compounds generated following equation (iv) in Section (III), or a compound of formula (III)), inhibit activity of the 5-$HT_3$ receptor. In certain embodiments, methods of inhibition of the 5-$HT_3$ receptor are in vitro methods. In certain embodiments, methods of inhibition of the 5-$HT_3$ receptor are in vivo methods.

In certain embodiments, the invention relates to methods of treating nausea, the methods comprising administering to a patient in need thereof an effective amount of a compound of formula (I), or a compound derived from formula (I) (such as a compound of formula (III)). In certain embodiments, the compound of formula (I), or a compound derived from formula (I), is co-administered with a chemotherapeutic agent. In certain embodiments, the patient is a cancer patient.

In certain embodiments, the invention relates to the use of a compound of formula (I) or a compound of formula (III) in the treatment of nausea, vomiting, motion sickness, or morning sickness.

EXEMPLIFICATION

The invention described generally herein will be more readily understood by reference to the following examples, which are included merely for purposes of illustration of certain aspects and embodiments of the present invention, and are not intended to limit the invention.

Example 1

Development of Decarboxylative Allylic Alkylation of Enaminones

Upon the initial discovery that catalytic decarboxylative allylic alkylation reactions in en-2-aminone substrates generate en-2-aminone products with all-carbon quaternary stereocenters and proceed in high enantioselectivities that are unprecedented for other carbocyclic substrates that lack substitution on the allylic fragment (depicted below), various reaction parameters were probed in order to optimize the reaction.

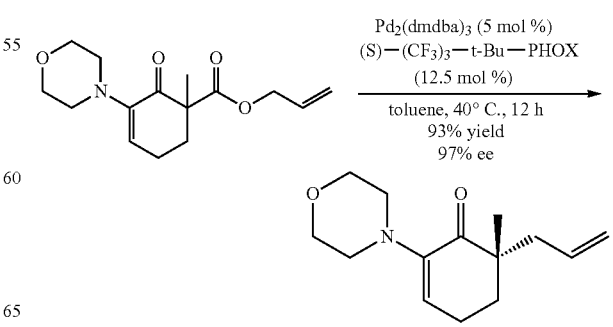

Solvent Survey

To develop general procedures for the decarboxylative allylic alkylation of enaminones, a survey of reaction solvents was conducted. The results are summarized in the table, below.

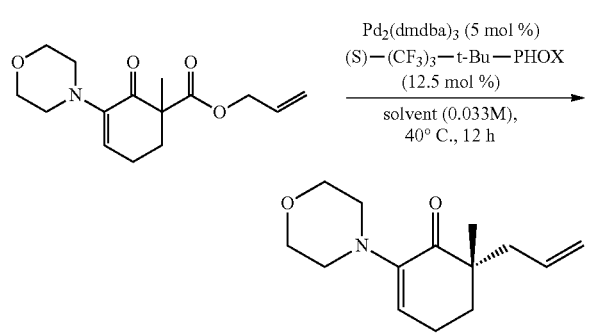

| solvent | % ee (chiral HPLC) | solvent | % ee (chiral HPLC) |
|---|---|---|---|
| 2:1 hex:tol | 94 | toluene | 97 |
| benzene | 95 | TBME | 95 |
| THF | 95 | CPME | 97 |
| DME | 95 | 2-MeTHF | 96 |
| dioxane | 94 | i-BuOAc | 92 |
| Et$_2$O | 97 | i-PrOAc | 96 |
| MeCN | 88 | EtOAc | 98 |

Temperature Effects

When the reaction was run at a lower temperature for a longer time, no improvement in enantioselectivity was observed.

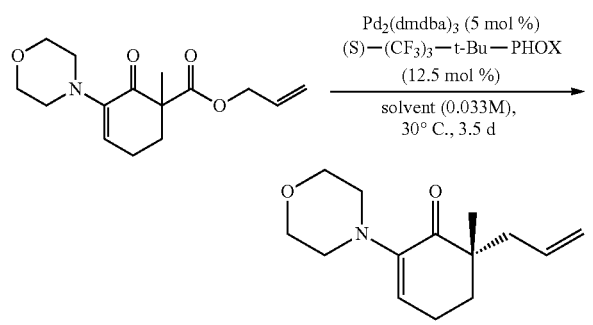

| solvent | % ee (chiral HPLC) |
|---|---|
| toluene | 94 |
| CPME | 97 |
| 2-MeTHF | 96 |
| i-PrOAc | 95 |
| EtOAc | 97 |
| Et$_2$O | 93 |

Ligand Survey

It was found that t-Bu-PHOX performed equally as well as the electron-poor analog used above. Ethyl acetate was a particularly promising solvent.

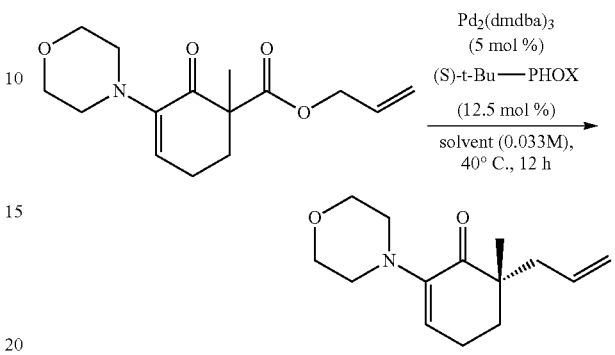

| solvent | % ee (chiral HPLC) |
|---|---|
| toluene | 94 |
| CPME | 98 |
| EtOAc | 98 |

The reaction was also run with low catalyst and ligand loadings to demonstrate its utility on scale. The results are summarized below.

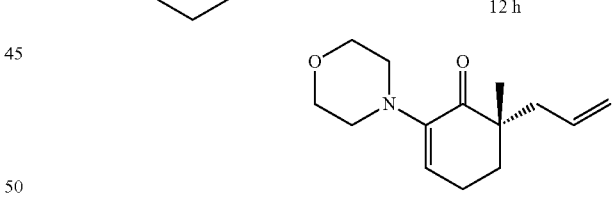

| scale (amount isolated product) | concentration (M) | catalyst loading (mol % Pd$_2$(dmdba)$_3$) | % yield | % ee (chiral HPLC or SFC) |
|---|---|---|---|---|
| 0.465 mmol (104 mg) | 0.033 | 5 | 95 | 98 |
| 5.41 mmol (1.19 g) | 0.1 | 1.67 | 94 | 99 |
| 12.3 mmol (2.69 g) | 0.33 | 0.5 | 93 | 98 |

Example 2

Procedures for Decarboxylative Allylic Alkylation of Enaminones

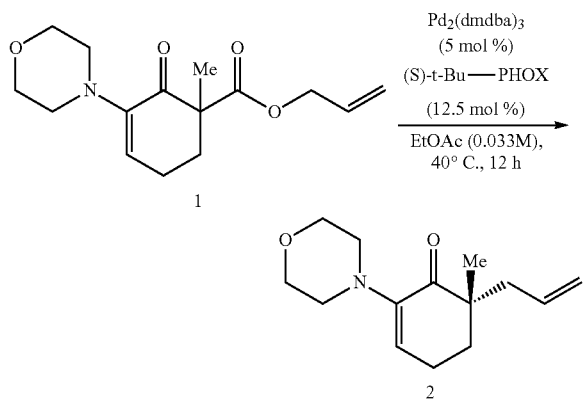

General Procedure A. In a nitrogen-filled glove box, Pd$_2$(dmdba)$_3$ (29.7 mg, 23.3 µmol, 0.050 equiv) was weighed into an oven-dried 20 mL scintillation vial equipped with a Teflon-lined stirbar. 10 mL EtOAc (distilled over K$_2$CO$_3$ and sparged for 2 h with argon) was added, resulting in a deep purple solution. (S)-t-BuPHOX (22.5 mg, 58.2 µmol, 0.125 equiv) was added, and the resulting mixture was stirred for 30 minutes at 40° C., resulting in a deep orange solution. A solution of substrate 1 (130 mg, 0.465 mmol, 1.00 equiv) in 4 mL EtOAc was added to the stirring catalyst mixture resulting in an olive-green solution. The reaction was sealed with a Teflon-lined cap and stirred for 12 h at 40° C., at which point the solution had reverted to a deep orange solution. The reaction was filtered through a silica plug (3×5 cm) with EtOAc as an eluent and concentrated in vacuo. The resulting yellow oil was purified by column chromatography (2×15 cm SiO$_2$, 5-10% acetone/hexanes) to yield enaminone 2 (104 mg, 0.437 mmol, 95% yield, 98% ee by chiral HPLC analysis) as a pale yellow oil.

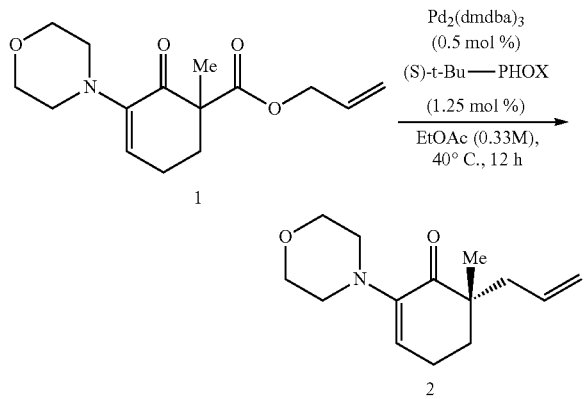

General Procedure B (low catalyst loading). In a nitrogen-filled glove box, Pd$_2$(dmdba)$_3$ (100 mg, 61 µmol, 0.005 equiv) was weighed into an oven-dried 100 mL round bottom flask equipped with a Teflon-lined stirbar. 30 mL EtOAc (distilled over K$_2$CO$_3$ and sparged for 2 h with argon) was added, resulting in a deep purple solution. (S)-t-BuPHOX (59 mg, 150 µmol, 0.013 equiv) was added, and the resulting mixture was stirred for 30 minutes at 23° C., resulting in a deep orange solution. A solution of substrate 1 (3.43 g, 12.3 mmol, 1.00 equiv) in 4 mL EtOAc was added to the stirring catalyst mixture resulting in an olive-green solution. The vial containing the substrate was rinsed with an additional 3 mL EtOAc, which was added to the reaction mixture. The reaction was sealed with a septum, removed from the glove box, and stirred for 12 h in a 40° C. oil bath, at which point the solution had reverted to a deep orange solution. The reaction was filtered through a silica plug (5×10 cm) with EtOAc as an eluent and concentrated in vacuo. The resulting yellow oil was purified by column chromatography (5×12 cm SiO$_2$, 5-10-20% acetone/hexanes) to yield enaminone 2 (2.72 g, 3.22 mmol, 94% yield, 99% ee by chiral HPLC analysis) as a pale yellow oil.

Application to an Array of Substrates

The reaction procedures outlined above were applied to a number of substrates. The substrates included electron-rich and electron-poor groups, alkyl, aralkyl, and halo groups. The reaction proved to be functional-group tolerant, providing products containing silyl ethers, ketones, esters, and nitriles in high yield and enantioselectivity.

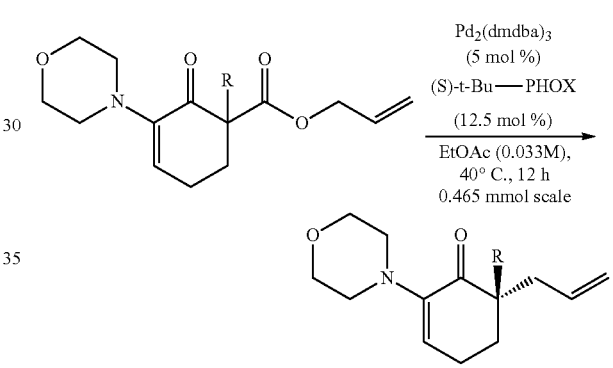

| R | % yield (isolated) | % ee (chiral HPLC or SFC) |
|---|---|---|
| Me | 95 | 98 |
| Et | 99 | 98 |
| Bn | 95 | 96 |
| 4-(CF$_3$)-Bn | 87 | 94 |
| 4-(OMe)-Bn | 99 | 96 |
| CH$_2$OTBS | 96 | 99 |
| CH$_2$CH$_2$OTBS | 93 | 99 |
| CH$_2$CH$_2$C(O)Me | 90 | 95 |
| CH$_2$CH$_2$CO$_2$Me | 98 | 98 |
| CH$_2$CH$_2$CN | 99 | 94 |
| F | 94 | 99 |

The reaction was also applied to substrates having alkyl-substitution at the beta-carbon of the cyclohexenone:

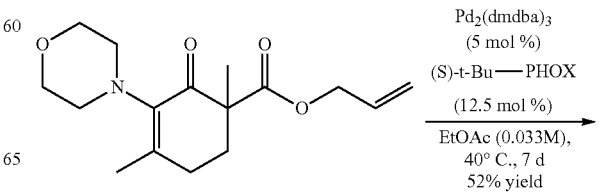

-continued

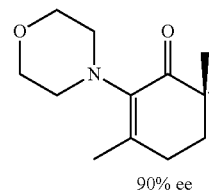

90% ee

The amino group of the enaminone substrate was also examined, and yielded the corresponding enantioenriched product:

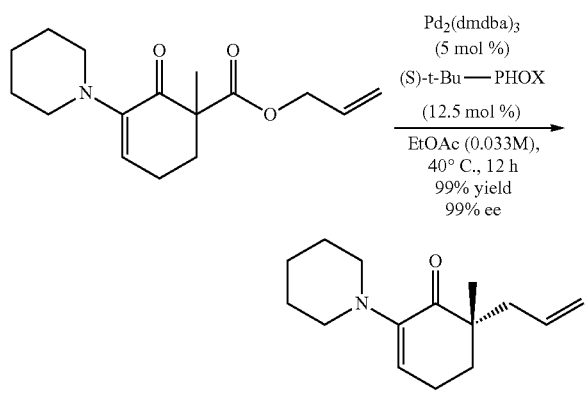

Smaller enaminone ring sizes were also successful substrates:

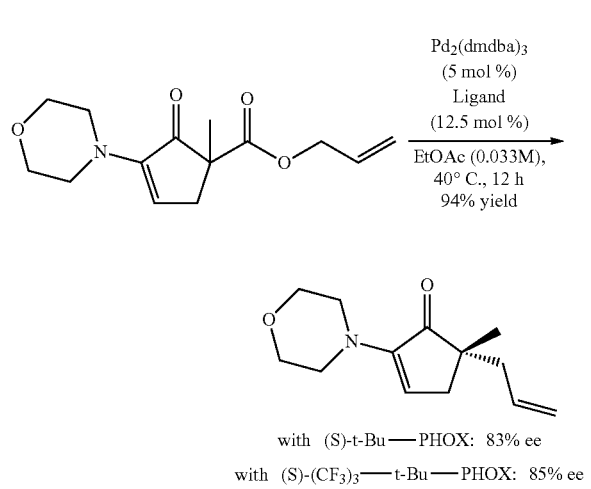

with (S)-t-Bu—PHOX: 83% ee
with (S)-(CF$_3$)$_3$—t-Bu—PHOX: 85% ee

Example 3

Reactions of α-Allyl Enaminone Products

The products generated by the methods of the invention have been elaborated into a number of useful synthetic compounds. The following transformations provide several examples of compounds that have been obtained from α-allyl enaminone products.

Hydrolysis:

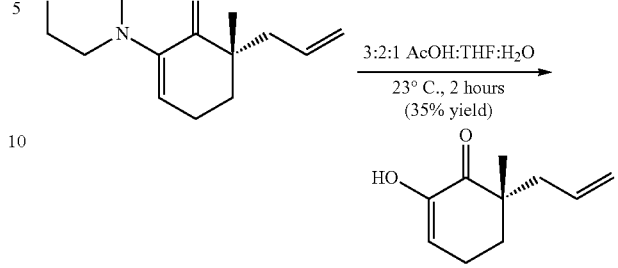

Reaction with Electrophiles:

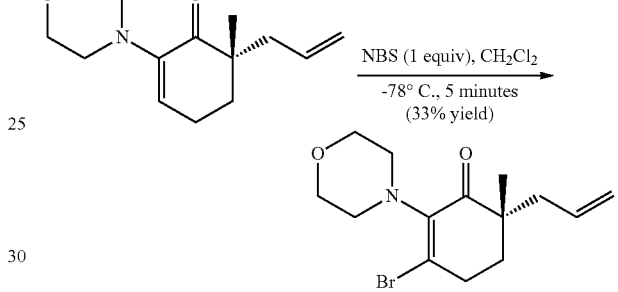

Indole Synthesis:

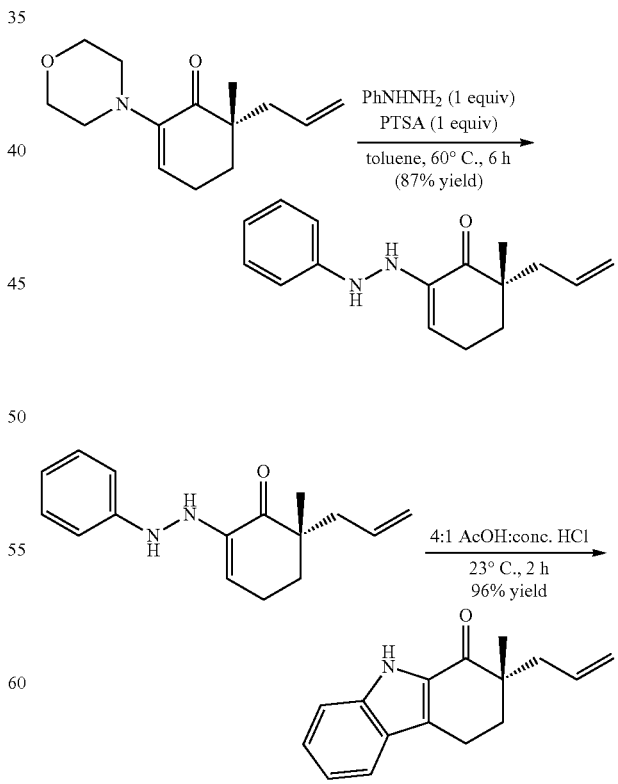

The two preceding reactions were also combined in a two-step process without purification of the intermediate. An exemplary synthetic protocol is shown below.

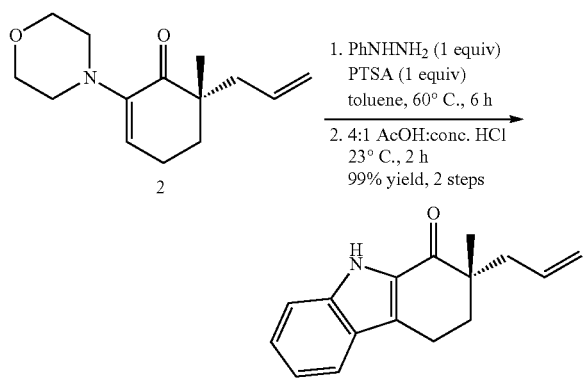

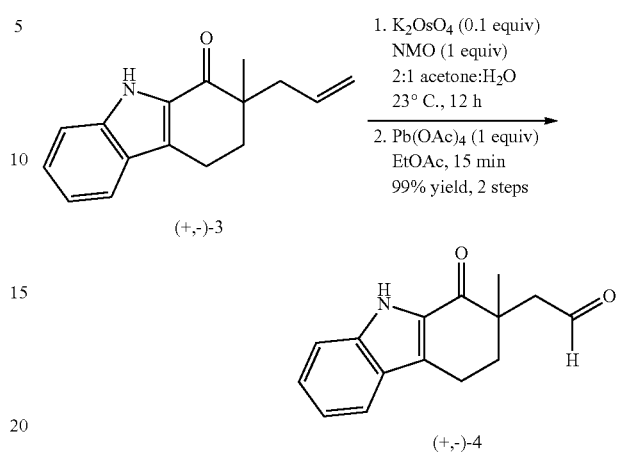

Synthesis of Indole 3: In a flame-dried 25 mL flame-dried round bottom flask equipped with a Teflon-lined stir bar under nitrogen, enaminone 2 (235 mg, 1.00 mmol, 1.00 equiv) was taken up in toluene (4 mL). Phenylhydrazine (108 mg, 1.00 mmol, 1.00 equiv) and p-toluenesulfonic acid monohydrate (190 mg, 1.00 mmol, 1.00 equiv) were added, and the reaction was heated to 60° C. The reaction turned from yellow to a bright orange brown. After 5 h, the reaction was complete by TLC analysis. The reaction was cooled to room temperature and diluted with EtOAc (20 mL) and saturated aqueous ammonium chloride (10 mL). The organic layer was separated, and the aqueous layer was extracted with EtOAc (2×20 mL). The combined organic portions were washed with brine (20 mL), dried over magnesium sulfate, filtered and concentrated in vacuo to afford a bright orange viscous oil. In a 50 mL round bottom flask equipped with a Teflon-lined stir bar, the crude product was taken up in a 4:1 mixture of acetic acid and water (10 mL). The reaction was stirred for 2 h, at which point the reaction was complete by TLC analysis. The reaction mixture was poured over ice (approx. 20 g). To the stirring ice mixture, 2.0 M aqueous KOH was added until the solution was at a pH of 10. The crude mixture was extracted with EtOAc (3×30 mL). The combined organic layers were washed with brine (30 mL), dried over magnesium sulfate, filtered and concentrated in vacuo. The resulting orange oil was purified by column chromatography (3×14 cm $SiO_2$, 10-20% EtOAc) to yield indole 3 (237 mg, 0.99 mmol, 99% yield over 2 steps) as a pale orange solid.

Example 4

Synthesis of a Library of Ondansetron Analogues

A library of analogues of Ondansetron was synthesized. Ondansetron (GSK Zofran) is a serotonin 5-$HT_3$ antagonist having a binding affinity of 4.9 nM to the 5-$HT_3$ receptor.

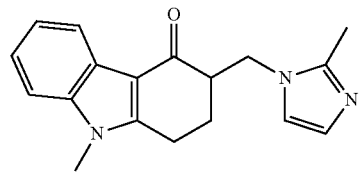

Ondansetron

From (+,−)-3, synthesized in Example 3, above, the following reactions were carried out.

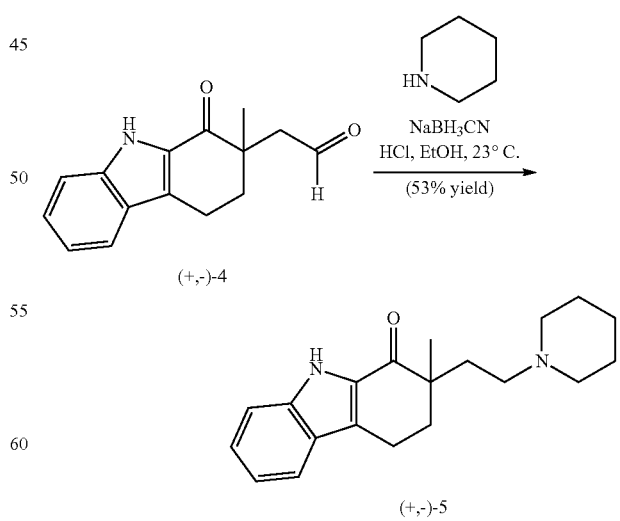

Synthesis of Aldehyde (+,−)-4: In a 25 mL round bottom flask equipped with a Teflon-lined stir bar, indole (+,−)-3 (167 mg, 0.700 mmol, 1.00 equiv) was taken up in 4:1 acetone:water (7 mL). To the stirring mixture, $K_2OsO_4$ (26 mg, 70 μmol, 0.1 equiv) and N-methylmorpholine N-oxide (164 mg, 1.40 mmol, 2.00 equiv) were added. The reaction was stirred for 12 h, at which point the reaction was complete by TLC. The reaction was quenched with 15 mL saturated aqueous $NaHSO_3$ and extracted with EtOAc (3×25 mL). The combined organic layers were washed with brine (15 mL), dried over magnesium sulfate, filtered and concentrated in vacuo to yield an orange oil. The crude product was taken up in EtOAc (7 mL) and Pb(OAc)$_4$ (341 mg, 0.77 mmol, 1.1 equiv) was added. After 15 minutes, the reaction was complete by TLC. The reaction was filtered through a Celite plug (3×5 cm) with EtOAc as an eluent and concentrated in vacuo. Aldehyde (+,−)-4 (167 mg, 0.69 mmol, 99% yield over 2 steps) was found to be pure without purification as a pale orange-yellow solid.

Reductive Amination, General Procedure C: To a solution of aldehyde (+,−)-4 (16 mg, 66 μmol, 1.0 equiv) in ethanol (0.7 mL) in a 2 mL vial equipped with a Teflon-lined stir bar, piperidine (5.9 mg, 70 μmol, 1.05 equiv) and sodium cyanoborohydride (12.5 mg, 199 μmol, 3.00 equiv) were added. Concentrated HCl was added dropwise until a pH of 3 was achieved (approximately 20 μL). The reaction was stirred for 15 minutes, at which point the reaction was complete by TLC. The reaction was diluted with 10 mL EtOAc and quenched with 5 mL saturated aqueous $K_2CO_3$. The phases were separated and the aqueous layer was extracted with EtOAc (2×5 mL). The combined organic layers were washed with brine (5 mL), dried over magnesium sulfate, and concentrated in vacuo. The resulting crude product was purified by preparative TLC (50:20:20:7:3 $CH_2Cl_2$: EtOAc: hexanes:MeOH:$Me_2$NH) to yield amine (+,−)-5 (11 mg, 53% yield) as a pale yellow oil.

The reductive amination procedure outlined above was utilized with a number of other amine reactants to generate the following compounds in yields ranging from 37% to 61%.

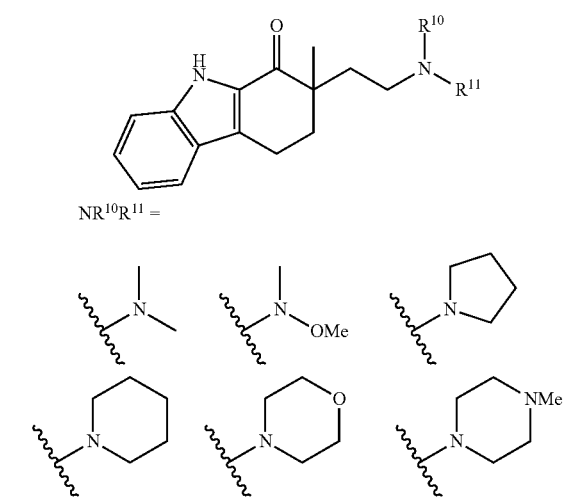

Example 5

Activity of Ondansetron Analogues

The patch clamp technique is a method used in electrophysiology to measure a change in voltage or current across a cell membrane in order to study the activity of ion channels in cells.

A glass micropipette (tip diameter ~1 mm) containing a conductive filament was inserted through the cell membrane. This allowed for the measurement of the flow of ions into the cell by measuring a change in current or voltage across the cell membrane.

Two such micropipettes were used, one to maintain a constant voltage across the cell membrane, while the other measured the current. Inhibition versus baseline 5-$HT_3$ activity was measured by applying a solution of agonist (serotonin), performing a wash, and then a solution mixture of agonist+inhibitor (10 mM).

*Xenopus laevis* (frog) oocytes transfected with mouse 5-HT3a mRNA were used in this study, due to size (~1 mm) and experimental tractability.

The results are summarized in the following table:

| —$NR^{10}R^{11}$ | % inhibition of mouse 5$HT_3$α (10 μM dose) |
|---|---|
| —N(CH₃)₂ | 76 ± 2, N = 8 |
| —N(CH₃)OMe | −3 ± 4 (no inhibition), N = 8 |
| pyrrolidinyl | 50 ± 2, N = 8 |
| piperidinyl | 33 ± 6, N = 8 |
| morpholinyl | 8 ± 4, N = 7 |
| N-methylpiperazinyl | 32 ± 4, N = 8 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control. The compounds, synthetic methods, and experimental protocols and results of U.S. application Ser. No. 13/680,582, filed Nov. 19, 2012, are hereby incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method for the preparation of a compound of formula (I):

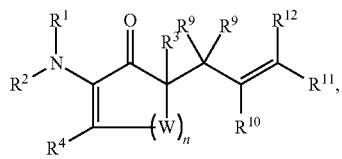

comprising treating a compound of formula (II):

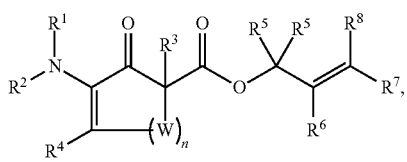

with a transition metal catalyst under alkylation conditions, wherein, as valence and stability permit, $R^1$ and $R^2$ are independently hydrogen or optionally substituted alkyl, aryl, aralkyl, heteroaryl, heteroaralkyl, alkenyl, or alkynyl; or $R^1$ and $R^2$ are taken together to form an optionally substituted heterocyclic ring;

$R^3$ is substituted or unsubstituted hydrogen, alkyl, aralkyl, aryl, heteroaralkyl, heteroaryl, alkenyl, alkynyl, or halo;

$R^4$ is hydrogen, halogen, alkyl, aralkyl, aryl, heteroaralkyl, heteroaryl, alkenyl, or alkynyl;

$R^5$, $R^6$, $R^7$, $R^8$, $R^9$, $R^{10}$, $R^{11}$, and $R^{12}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;

W is $CR^{13}R^{13}$, O, S, or $NR^{14}$;

$R^{13}$ is selected, independently for each occurrence, from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, arylalkoxy, heteroaralkyl, carbocyclylalkyl, and heterocyclylalkyl;

$R^{14}$ is independently selected for each occurrence from hydrogen, alkyl, aryl, aralkyl, heteroaryl, heteroaralkyl, alkenyl, or alkynyl;

wherein $R^2$ and $R^4$ may combine with the atoms to which they are attached to form an optionally substituted 4-9 membered heterocyclic ring, $R^4$ and an occurrence of $R^{13}$ may combine with the carbons to which they are attached to form an optionally substituted 3-8 membered ring, $R^4$ and an occurrence of $R^{14}$ may combine with the atoms to which they are attached to form an optionally substituted 4-8 membered heterocyclic ring, two occurrences of $R^{13}$ may combine with the carbons to which they are attached to form a 3-8 membered ring, or an occurrence of $R^{13}$ and an occurrence of $R^{14}$ may combine with the atoms to which they are attached to form an optionally substituted 4-8 membered heterocyclic ring; and n is an integer from 1-4.

2. The method of claim 1, wherein $R^5$, $R^6$, $R^7$, $R^8$, $R^9$, $R^{10}$, $R^{11}$, and $R^{12}$ are each independently selected for each occurrence from hydrogen, halogen, cyano, alkyl, alkoxy, alkylthio, amide, amine, aryloxy, and arylalkoxy.

3. The method of claim 1, wherein $R^3$ is selected from optionally substituted alkyl, aryl, aralkyl, haloalkyl, and hydroxyalkyl.

4. The method of claim 1, wherein W at each occurrence is $CR^{13}R^{13}$ and n is an integer from 1-3; and wherein $R^{13}$ is selected, independently for each occurrence, from hydrogen, halogen, cyano, alkyl, alkoxy, alkylthio, amide, amine, aryloxy, and arylalkoxy.

5. The method of claim 1, wherein $R^1$ and $R^2$ taken together form an optionally substituted heterocyclic ring.

6. The method of claim 1, wherein the transition metal catalyst comprises a transition metal selected from palladium, nickel, and platinum.

7. The method of claim 6, wherein the transition metal catalyst comprises $Pd_2(dba)_3$ or $Pd_2(pmdba)_3$.

8. The method of claim 7, wherein the transition metal catalyst is used in an amount from about 0.1 mol % to about 20 mol % total palladium relative to the compound of formula (II).

9. The method of claim 1, wherein the transition metal catalyst further comprises an enantioenriched phosphine ligand.

10. The method of claim 9, wherein the enantioenriched phosphine ligand is a phosphinooxazoline ligand.

11. The method of claim 10, wherein the phosphinooxazoline ligand is selected from (S)—$(CF_3)_3$-tBuPHOX and (S)-tBuPHOX.

12. The method of claim 10, wherein the ligand is used in an amount selected from 0.25 mol % to about 25 mol % relative to the compound of formula (II).

13. The method of claim 1, wherein the compound of formula (I) is enantioenriched.

* * * * *